United States Patent
Kruecker et al.

(10) Patent No.: US 11,963,826 B2
(45) Date of Patent: *Apr. 23, 2024

(54) RECONSTRUCTION-FREE AUTOMATIC MULTI-MODALITY ULTRASOUND REGISTRATION

(71) Applicant: KONINKLIJKE PHILIPS N.V., Eindhoven (NL)

(72) Inventors: Jochen Kruecker, Andover, MA (US); Amir Mohammad Tahmasebi Maraghoosh, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,654

(22) Filed: Jul. 15, 2022

(65) Prior Publication Data
US 2022/0346757 A1 Nov. 3, 2022

Related U.S. Application Data

(63) Continuation of application No. 15/310,925, filed as application No. PCT/IB2015/052383 on Apr. 1, 2015, now Pat. No. 11,419,583.

(Continued)

(51) Int. Cl.
*A61B 8/08* (2006.01)
*A61B 5/06* (2006.01)
(Continued)

(52) U.S. Cl.
CPC ............ *A61B 8/5261* (2013.01); *A61B 5/062* (2013.01); *A61B 5/066* (2013.01); *A61B 8/0841* (2013.01);
(Continued)

(58) Field of Classification Search
CPC ...... A61B 2034/2051; A61B 2090/364; A61B 2090/367; A61B 2090/378; A61B 34/20;
(Continued)

(56) References Cited

U.S. PATENT DOCUMENTS 6,167,296 A 12/2000 Shahidi
2007/0019861 A1* 1/2007 Zwanger .................. G06T 7/11
382/128

(Continued)

FOREIGN PATENT DOCUMENTS

JP 09-299371 * 11/1997
WO 2012117381 A1 9/2012

OTHER PUBLICATIONS

Solberg et al., "Freehand 3D Ultrasound Reconstruction Algorithms—A Review", Ultrasound in Med & Biol., vol. 33, No. 7, pp. 991-1009, 2007. (Year: 2007).*

(Continued)

*Primary Examiner* — Katherine L Fernandez (57) ABSTRACT

Image co-registration entails: emitting energy, and responsively and dynamically acquiring images, the acquired images having a given dimensionality; selecting, repeatedly, and dynamically with the acquiring, from among the acquired images and, as a result of the selecting, changing, repeatedly, and dynamically, membership in a set of images of the given dimensionality; and, synchronously with the change, dynamically and iteratively registering the set to an image having a dimensionality higher than the given dimensionality. The co-registration is realizable with an imaging probe for the acquiring, and a tracking system for tracking a location, and orientation, of the probe, the registering being specialized for the acquiring with the probe being dynamically, during the acquiring, any one or more of angulated, rotated and translated. The registering is initialized by individual transformations of members of the set, but (Continued)

without need for reconstruction, of the set into an image of dimensionality higher than the given dimensionality, that derives, from the set, additional pixels external to the members.

18 Claims, 4 Drawing Sheets

Related U.S. Application Data

(60) Provisional application No. 61/994,308, filed on May 16, 2014.

(51) Int. Cl.
*A61B 34/20* (2016.01)
*A61B 90/00* (2016.01)

(52) U.S. Cl.
CPC ...... *A61B 34/20* (2016.02); *A61B 2034/2051* (2016.02); *A61B 2090/364* (2016.02); *A61B 2090/367* (2016.02); *A61B 2090/378* (2016.02)

(58) Field of Classification Search
CPC ....... A61B 5/062; A61B 5/066; A61B 8/0841; A61B 8/5261
See application file for complete search history.

(56) References Cited

U.S. PATENT DOCUMENTS

| | | | |
|---|---|---|---|
| 2009/0054776 A1* | 2/2009 | Sasaki | A61B 8/483 600/443 |
| 2010/0208963 A1* | 8/2010 | Kruecker | G06T 3/0081 382/131 |
| 2010/0286517 A1 | 11/2010 | Kamen et al. | |
| 2016/0100821 A1* | 4/2016 | Eggers | A61B 8/54 600/424 |
| 2016/0113632 A1* | 4/2016 | Ribes | A61B 8/5269 600/440 |

OTHER PUBLICATIONS

English translation of JP 9-299371 (Year: 1997).*
Wein, et al., "Automatic CT-ultrasound registration for diagnostic imaging and image-guided intervention", Medical Image Analysis, Oxford University Press, vol. 12, No. 5, Oct. 1, 2008, pp. 577-585.
Mercier, et al., "A Review of Calibration Techniques for Freehand 3-D Ultrasound Systems", Ultrasound in Medicine and Biology, New York, NY, vol. 31, No. 4, Apr. 1, 2005, pp. 449-471.

* cited by examiner

RECONSTRUCTION-FREE AUTOMATIC MULTI-MODALITY ULTRASOUND REGISTRATION

This application is a continuation of U.S. Ser. No. 15/310,925 filed on Nov. 14, 2016, and issued as U.S. Pat. No. 11,419,583, which in turn is the U.S. National Phase application under 35 U.S.C. § 371 of International Application No. PCT/IB2015/052383, filed on Apr. 1, 2015, which claims the benefit of U.S. Provisional Application Ser. No. 61/994,308, filed May 16, 2014. These applications, and issued patent, are hereby incorporated by reference herein.

FIELD OF THE INVENTION

The present invention relates to co-registering images and, more particularly, to registering an N-dimensional image to a set of images of lesser dimension.

BACKGROUND OF THE INVENTION

Automatic registration of medical ultrasound (US) and computed tomography (CT) imaging can benefit diagnostic as well as interventional procedures. Three-dimensional (3D) images are typically acquired in both modalities. An approach to US-CT registration in commonly-owned International Publication No. WO 2012/117381 to Kadoury et al. ("Kadoury") involves reconstructing a three-dimensional (3D) US volume based on a spatially tracked 2D US "sweep", followed by automatic 3DUS-CT registration.

SUMMARY OF THE INVENTION

What is proposed herein below is a further development of the Kadoury methodology. As in Kadoury, registration is achieved with a 3D, pre-existing image of a modality other than US, such as CT or magnetic resonance imaging (MRI). However, the preparatory step of reconstruction from the US 2D frames is omitted. Although spatial tracking is still used, it is employed to align the frames as an integral unit. As in Kadoury, a transformation is performed to realize the co-registration. However, the US acquisition and registration is done dynamically, repeatedly and progressively, commencing with a sparse set of acquired US frames. Any preparation for an instance of the registration is thus, with respect to US, reconstruction-free. The sparseness results from dynamic selectivity based on image quality and inter-frame distance. The duration of the procedure is accordingly shortened. In particular, the reconstruction of 3DUS from 2DUS slices takes time; the user needs to review the 3DUS and needs to redo the sweep if the image quality is not adequate; the "sweep" itself takes training and practice in order to create good volume image quality; and the actual registration task can only start once the reconstruction is done and accepted, causing additional delay in the processing chain. Three-dimensional (3D) US probes can alleviate some of the reconstruction issues; however, 3DUS probes are expensive, not widely available, and limit the size of the volume to be acquired. What is proposed herein addresses these concerns, among others.

In particular, an exemplary image co-registration device includes an image acquisition processor configured for emitting energy, and responsively and dynamically acquiring images. The acquired image has a given dimensionality.

Further included is an image selection processor configured for selecting, repeatedly, and dynamically with the acquiring, from among the acquired images and, as a result of the selecting, changing, repeatedly, and dynamically, membership in a set of images of that dimensionality.

Also included is an image co-registration processor configured for, synchronously with the change, dynamically and iteratively registering the set to an image having a dimensionality higher than the given dimensionity.

Details of the novel, reconstruction-free automatic multi-modality US registration technology are set forth further below, with the aid of the following drawings which are not drawn to scale.

DETAILED DESCRIPTION OF EMBODIMENTS

An integrated framework provides an accurate and real-time updated transformation chain to connect free-hand two-dimensional (2D) ultrasound (US) images to a pre-acquired 3D reference volume from another modality. In this disclosure, "real-time" means without intentional delay, given the processing limitations of the system and the time required to accurately perform the function.

Present embodiments will be described herein below in terms of on-the-fly registering a pre-operative image volume with a set of intra-operative two-dimensional images whose members are progressively and dynamically acquired for selective admission into the set; however, the systems and methods in accordance with the present principles can be applied to registrations between any of pre-operative, intra-operative, and post-operative images for monitoring, interventional procedures and/or diagnostic applications.

The embodiments also will be described in terms of medical systems and instruments; however, the teachings of the present invention are much broader and are applicable to any instruments employed in dynamically co-registering images of different dimensions. The co-registration may improve dynamically and visibly, subject to a stopping criterion or stopping criteria. Such instruments may be employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The region of interest may be a bodily organ, such as the liver or kidney for example. The procedures may be carried out on a specimen as well as a live animal or human subject or patient, and, more generally, on any object. The elements depicted in the figures may be implemented in various combinations of hardware and software and provide functions which may be combined in a single element or multiple elements. The present principles may be applied for guidance of many interventional or surgical procedures that need registration of the patient with a prior medical image (e.g., biopsy, ablation, embolization, drainage, etc.). These principles may also be applied in diagnostic applications that employ multi-modality registration and may not involve interventional procedures. For example, since ultrasound and CT provide complementary diagnostic information, it may be beneficial to register these two modalities to ensure that the same lesion is being evaluated in both images.

The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc. In particular and by way of example, an image acquisition processor as a part of a computer, or scanner incorporating a computer, performs calculations, and other manipulations of data, for issuing energy and responsively acquiring an image. This processor may share circuitry, other hardware and/or software with other application-specific processors. One or more processors may be implemented as one or more integrated circuits.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block and schematic diagrams presented herein below represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

Figure 1:
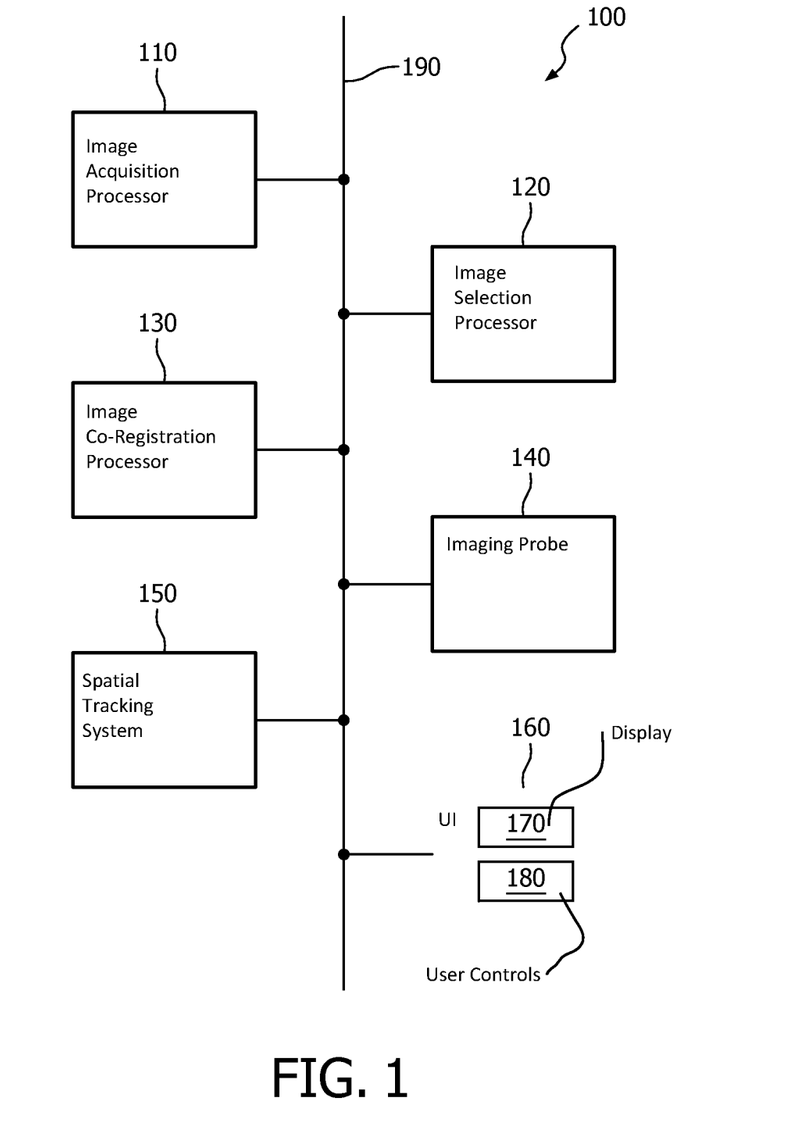
FIG. 1 is a schematic diagram of an exemplary reconstruction-free automatic multi-modality US registration device, in accordance with the present invention.

FIG. 1 shows, by illustrative and non-limitative example, a reconstruction-free automatic multi-modality US registration device, or "image co-registration device", 100. As mentioned herein above, an exemplary embodiment features on-the-fly registering of a pre-operative image volume with a set of intra-operative two-dimensional images whose members are progressively and dynamically acquired for selective admission into the set.

The device 100 includes an image acquisition processor 110, an image selection processor 120, and an image co-registration processor 130. It may further include a imaging probe 140, a spatial tracking system 150, and a user interface 160 that comprises a display 170, which can include multiple screens, and user-actuatable controls 180. An example of a spatial tracking system is the Aurora™ electromagnetic (EM) tracking system from NDI. Various types of electromagnetic locator systems can be utilized. In one example, an (EM) field generator has antennas at different orientations. A tracking sensor fixed to the probe 140 picks up the signals from the antennas at the various orientations. From their relative signal characteristics, e.g., relative signal strength, relative phase, etc., the location of the sensor relative to the antennas is determined. In another embodiment, the sensor has receiving coils or antennas with different orientations. In one embodiment, the sensor is connected with a localizer processor by wires running down the handle of the probe 140. In another embodiment, a wireless communication path is used. The components 110-180 of the device 100 are communicately connected 190, the connection of each to the others being by wireline and/or wireless.

Figure 2:
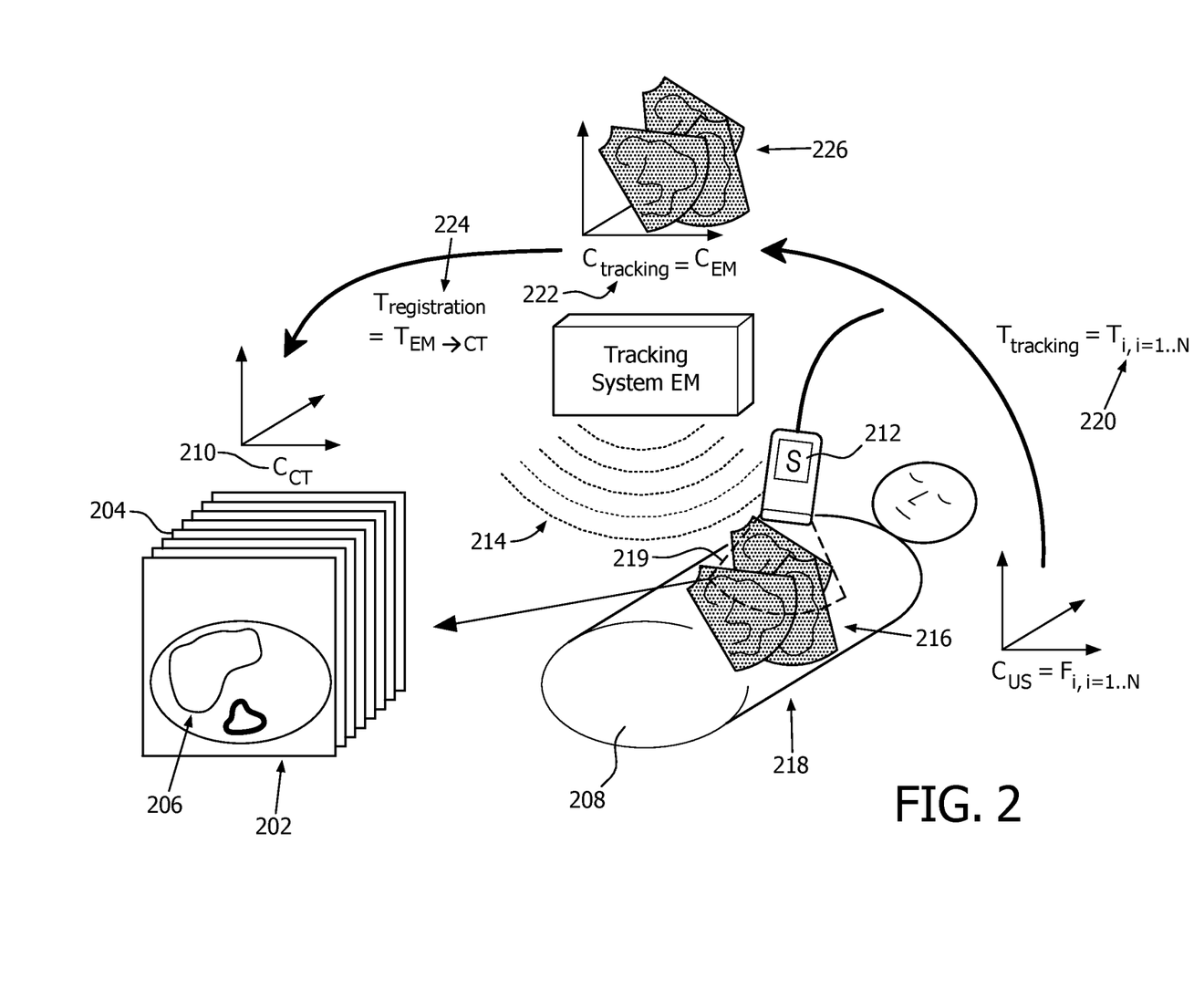
FIG. 2 is a conceptual diagram of on-the-fly, progressive image co-registration, in accordance with the present invention.

FIG. 2 provides a conceptual depiction of co-registration serving as an example of what is proposed herein. A CT system (not shown) acquires a 3D image 202, slices 204 of which are shown. A bodily organ 206 of interest of a patient 208 to undergo examination is segmented. This is done automatically via a model of the organ 206. Alternatively, it can be done manually via user maneuvering of a cursor via the controls 180 interactively with what is viewed on the display 170. The segmented organ 206 resides in a CT coordinate system 210 $C_{CT}$. Points on the surface of the organ 206 are designated to form a point cloud. For greater registration accuracy, the point cloud is formed by densely sampling the organ surface. A mesh model of the organ might automatically provide the surface vertices, or other automatic surface sampling might be done. Or the sampling can manually be done interactively.

In fixed spatial relation, as by physical attachment or incorporation, with the probe 140 is a tracking sensor 212 which is part of the tracking system 150. The tracking system 150 further includes an EM field generator (not shown in the figures). A field 214 generated excites the tracking sensor 212, causing production of a signal indicative of the location and orientation of the probe 140. The location and orientation are representable by six parameters—three for location and three for orientation.

With the pre-operative CT imaging and CT-specific point cloud having been prepared, the US probe 140 is usable intra-operatively to examine the same organ 206 in the same patient 208 now to undergo US examination. The probe 140 is positioned for acquisition of 2DUS images 216 of a region of interest (ROI) 218 containing the organ 206. The images or frames 216 are acquired from correspondingly different locations within an object subject to examination. They are obtained using different rotations, translations and/or angulations of the probe 140. This step is very similar to conventional "survey" scanning of the ROI 218 typically performed during diagnostic exams or before interventional procedures, and requires little or no training. When being performed manually by the user, it offers an advantage over a conventional sweep which does, for effectiveness, require skill and typically training and experience. In addition, there is no need for the starting and stopping of image acquisition that requires synchronization with a second operator, i.e., at the console or workstation. Alternatively, the maneuvering can be done automatically. An example would be a robotic arm controlling movement of the probe 140. The co-registering is specialized for the acquiring of US images with the probe 140 being dynamically, during the acquiring, any one or more of angulated, rotated and translated.

The image acquisition processor 110 stores in a memory (not shown) tracking sensor location and tracking sensor orientation values specific for each acquired frame 216. This stored imaging data could be used to derive additional pixels 219 external to the member frames; however, what is proposed herein dispenses with the need to engage in such US reconstruction. Rather than using the information to reconstruct a 3DUS image, the frames 216 are, while retained in situ with respect to each other for anatomical correctness, treated as a unitary whole for an affine transformation to match into registry with the CT volumetric image 202. Thus, an individual transformation 220 $T_i$ of an individual frame 216 $F_i$ from the frame coordinate system, is specific to the corresponding stored location and orientation values. The transformations 220 $T_i$ are into a tracking coordinate system 222 $C_{tracking}$. The transformations 220 $T_i$ are separately chained to a transformation 224 $T_{registration}$, determinable as described herein below, between the tracking coordinate system 222 $C_{tracking}$ and the CT coordinate system 210 $C_{CT}$.

By foregoing reconstruction of the US frames 216, the time needed for reconstruction is saved. Thus, the volume that can reasonably be covered by the scan is increased. Motion and deformation artefacts characteristic of such reconstructions, and other limitations of image quality, are avoided. Also avoided is the need for post-reconstruction review by the user for ensuring adequate image quality, and the associated additional time delay.

Only a sparse set 226 of the acquired frames 216 is utilized for co-registration with the 3D image 202. This creates a sparse representation of the 3DUS image space, as opposed to the conventionally fully sampled reconstruction of a sweep. The sparse 3D US representation is the collection of individual 2DUS image frames 216, together with the tracking poses. Thus, the set 226 is in effect a tracked cineloop of 2DUS images that have been selected from among the stream of incoming acquired images.

Each individual 2D US image frame 216 is processed immediately, and is added to the registration process on the fly if it passes basic automatic quality tests. More particularly, the frame 216 is examined for its content, and measurement is made of the spatial proximity of the frame 216 to other frames that have already passed the test(s) and have thus been added to the set 226. Set membership selection can entail the application of multiple thresholds, discussed herein below, that are determinable through analysis, empirical experience or some combination of the two.

This selection process can use an algorithm for selecting which tracked images 216 have sufficient information to be used for registration. Some of the criteria are, for example, as follows. If several frames 216 are obtained in almost the exact same spatial location, only one of the frames is kept. If the mean image intensity in a significant fraction of the image 216 is below a threshold, it is likely obtained with insufficient contact with the skin of the patient 208, or is degraded by shadowing, and is to be discarded. If the entropy or the maximum gradient is below a threshold, the image 216 likely does not contain sufficient information for registration purposes, and is to be discarded. Low maximum gradient, for example, indicates likely insufficient "edge" information.

Once a frame 216 has been selected for admission into the set 226, the previously acquired frames not in the set can be deleted to increase available storage.

A point cloud is sparsely determined for the set 226, e.g., a few or several points per frame 216. The points are automatically chosen on the automatically segmented 2D surface of the organ 206. For example, the points may be chosen according to equal spacing along the segmented surface. The US point cloud can be matched to corresponding points in the CT-specific point cloud, to bring the the US images 216 into registry with CT image. An iterative closest points (ICP) algorithm, or one of its derivatives, can be used for this purpose. An exemplary algorithm is described in commonly-owned U.S. Patent Publication No. 2012/0027277 to Vik et al (hereinafter "Vik").

The output of the ICP is the transformation 224 $T_{registration}$. As mentioned herein above, the transformation 224 $T_{registration}$ is chained separately to the individual transformations 220 $T_i$. The separate chains correspond to the respective frames 216. For each frame 216, the associated chain of transformations is applied to bring the frame into registration with the 3DCT image 202.

US acquisition, selection for the set 226, update of the transformation chain, and user feedback all occur dynamically and repeatedly in real time, until halted automatically or by the user. As described herein, the entire procedure is executable without need for user intervention.

The transformed frames 216 may be presented on the display 170, fused with the 3DCT image 202 or side by side. A side by side presentation can be done on one screen or respectively more than one screen. Alternatively, the feedback could be a number quantifying registration accuracy, or could be an audible beep when the algorithm determines that the registration quality suffices or cannot be further improved.

Thus, the user may, for instance, enter a halt instruction interactively while viewing the display 170, which may show fusing of the images or the above-mentioned number quantifying registration accuracy. On the other hand, the user may abort and restart if no acceptable quality is achieved within a reasonable time.

There may exist an automatic determination of when to end the iterative co-registration. The test may be whether the improvement via another iteration would be other than negligible, as in step 260 of Vik. As another example, the criterion may be whether the mean distance between the corresponding points of US and CT point clouds is below a threshold.

In an alternative embodiment, the current respiratory or cardiac phase (i.e., natural body cycle phase) of the patient 208 can be detected. Detection can be via an additional tracking sensor attached to the sternum of the patient 208. The sensor would move cyclically with the body cycle. Each frame 216 in the set 226 can thus also be associated with a particular phase of the cycle. Frames 216 can be grouped by phase (e.g., inhale, mid, exhale). Thus, instead of a single set 226, a set exists for each phase. The member frames 216 of a set are all associated with the same phase. Each instance of co-registration between CT and US pertains to the then-current phase. Accurate registrations throughout the entire body cycle can accordingly be computed and subsequently applied during the procedure.

In the above discussion, members of the set 226 have a dimensionality of two and the CT volumetric image 202 has a dimensionality of three.

However, this is not a limitation.

It is within the intended scope of what is proposed herein for, as an example, the member dimensionality to be one and the CT image dimensionality to be two.

Optionally too, instead of each iteration of the co-registration being preceded by merely adding a new member to the set 226, new members may replace existing members of the set. Such an iteration would serve to replace a member, whose image quality is borderline, with the current frame 216 if it is sufficiently spatially proximate and of sufficiently higher image quality. Therefore, more generally speaking, a result of the selecting, from among acquired frames 216, changes membership in the set 226.

Figure 3:
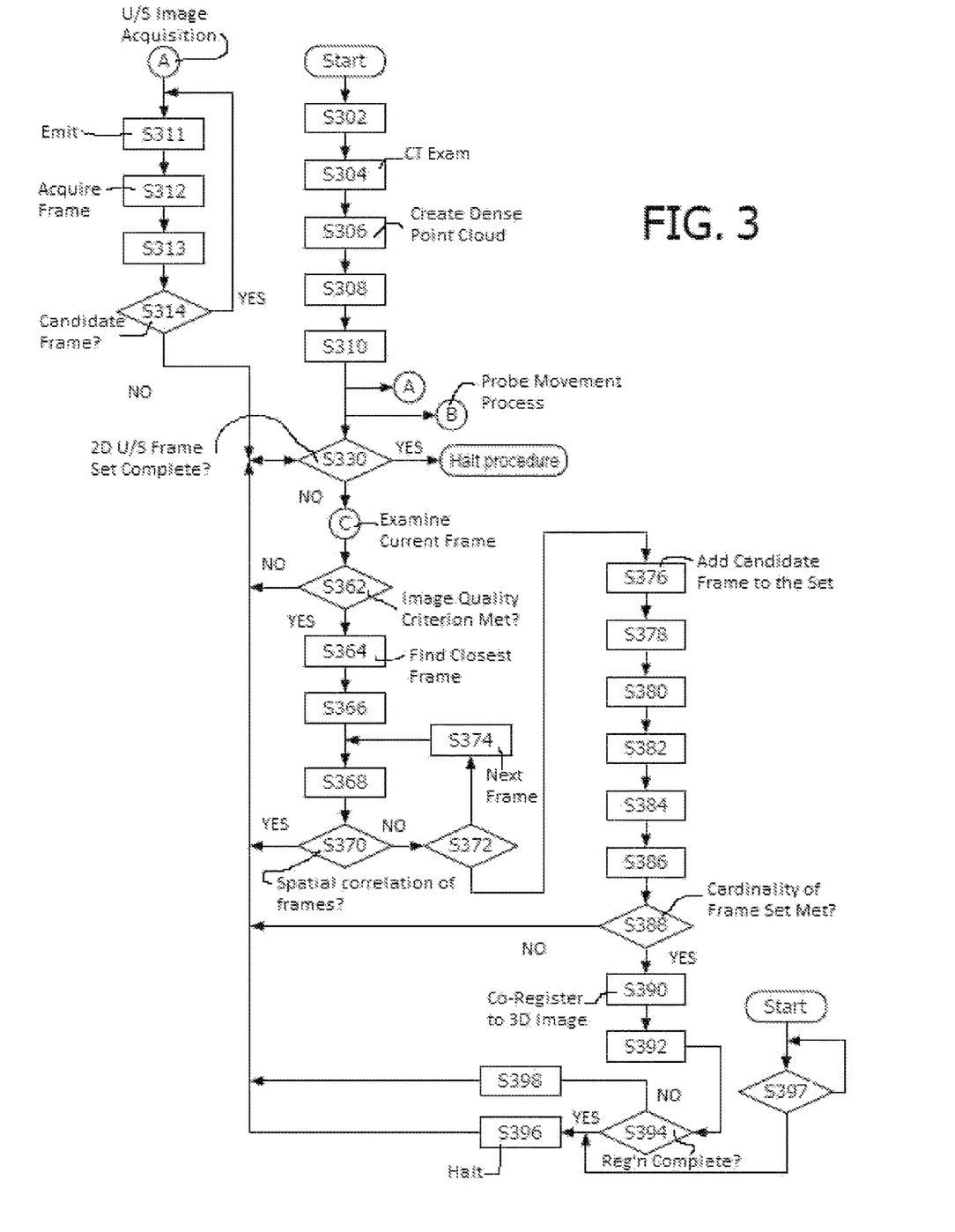
FIG. 3 is a flow chart exemplary of reconstruction-free automatic multi-modality US registration, in accordance with the present invention.

A flow diagram representative of a version of the image co-registration procedure 300 is shown in FIG. 3.

An organ of interest is chosen (step S302). The CT examination of the ROI 218 is performed (step S304).

A dense point cloud on the surface of the organ 206 is created (step S306). The US probe 140 is provided (step S308).

The probe 140 is placed on the skin of the patient 208 and auto-registration is commenced, as by user actuation of the user controls 180 (step S310).

A subprocedure A is launched in which ultrasound is emitted (step S311). Responsively, a frame is acquired (step S312). The location and orientation of the tracking sensor 212 are stored (step S313). If the acquired frame is to be considered a candidate for selection to be admitted to the set 226 (step S314), return is made to the ultrasound emitting step S311; otherwise, selection of acquired frames for admission to the set 226 is halted, as described herein below.

Concurrently, a probe movement process B is launched or performed manually by the user. If, and while, it involves angulation (step S318), the probe 140 is angulated (step S320). If, and while, it involves rotation (step S322), the probe 140 is rotated (step S324). If, and while, it involves translation (step S326), the probe 140 is translated (step S328). Any combination of the three types of movements can be performed simultaneously.

If no next frame 216 is to be chosen, from among the acquired frames, for candidacy with respect to admission into the set 226 (step S330), the procedure 300 is complete.

Otherwise, if a next frame 216 is to be to be made a candidate (step S330), that frame 216, as the current frame, is examined for its content (step S332). In particular, if entropy is to be measured (step S334), the entropy is measured (step S336). An example of an entropy measurement is found in paragraph [0038] of U.S. Patent Publication No. 2012/0075440 to Ahuja et al., paragraphs [0037] and [0038] being incorporated herein by reference. If the measured entropy meets a predetermined entropy threshold $T_E$ which serves as an image quality metric (step S338), an image quality criterion for the current frame 216 is met (step S340). Otherwise, if the measured entropy does not meet $T_E$ (step S338), the image quality criterion for the current frame 216 is not met (step S342). If, on the other hand, entropy is not to be measured (step S334), but the image gradient is to be measured (step S344), an image gradient calculation operates on the current frame (step S346). The calculation entails measurement throughout the frame 216 in multiple, e.g., four, directions to determine the maximum gradient. An example of image gradient measurement is found in paragraph [0026] of commonly-assigned U.S. Patent Publication No. 2009/0263039 to Bruls et al., paragraphs [0024]-[0026] being incorporated herein by reference. If the measured maximum gradient meets a predetermined gradient threshold which serves as an image quality metric (step S348), the image quality criterion for the current frame 216 is met (step S340). If, on the other hand, the measured maximum gradient does not meet the gradient threshold (step S348), the image quality criterion for the current frame 216 is not met (step S342). Finally, if neither the entropy nor maximum gradient is to be measured (steps S334, S344), the mean image intensity of the current frame 216 is calculated (S350). The mean image intensity can be equated to a measurement of the mean pixel intensity. Firstly, processing points to a first portion of the current frame 216 (step S352). If the mean image intensity for the current portion fails to meet a predetermined image intensity threshold (step S354), and the fractional amount of the portion exceeds a fractional amount threshold specific to the measured mean intensity (step S356), the image quality criterion for the current frame 216 is not met (step S342). If, however, despite the mean image intensity for the current portion failing to meet the predetermined image intensity threshold (step S354), the fraction amount of the portion does not exceed the fractional amount threshold (step S356), query is made as whether a next portion to be examined for the current frame exists (step S358). If no such next portion exists (step S358), the image quality criterion for the current frame is met (step S340). Otherwise, if a next portion exists (step S358), processing points to that next portion as the current portion (step S360) and branches back to step S354. Although the image quality tests are in this example mutually exclusive, any two or more of them can be combined as a multiple-part test.

If it is determined that the image quality criterion is not met (step S362), processing returns to step S330.

If, on the other hand, the image quality criterion is met (step S362), the spatially closest frames 216 in the set 226 to the current frame 216, i.e., current candidate frame, are found (step S364). This measure of proximity can be, for example, for a member frame, the maximum distance between a point on the perimeter of the current frame 216 and the corresponding point on the perimeter of the member frame. Thus, the spatially closest frames are the ones that exceed a predetermined image frame distance threshold $T_{FD}$. Processing points to a first member frame from among the spatially closest (step S366). This member frame serves as the current member frame.

The current member frame is cross-correlated with current candidate frame (step S368), over a given search area.

If the maximum $\rho_{max}$ of the cross-correlation function exceeds a correlation threshold $T_\rho$ (step S370), the candidate frame is superfluous with respect to the existing set 226. In particular, the candidate frame and current member frame have respective content that is too similar for allowing both frames, at such spatial proximity, to be in the set 226. The selection process resumes at step S330.

If, on the other hand, $\rho_{max}$ does not exceed $T_\rho$ (step S370), query is made as to whether a next candidate frame exists from among the selected closest frames in the set 226 (step S372). If a next candidate exists (step S372), that next candidate is made the current candidate (step S374) and return is made to the cross-correlation step S368. Otherwise, if no next candidate exists (step S372), the candidate frame is added to the set 226 (step S376). The location information stored in step S313 is retrieved for the frame which is now newly a member of the set (step S378). The orientation information stored in step S313 is retrieved (step S380). Based on the retrieved information, the current member frame 216 $F_i$ is transformed into tracking space by the transformation 220 $T_i$ (step S382). The organ of interest 206 is segmented, and points on the surface of the organ are selected (step S384). The selected points are added to the iteratively growing sparse US organ-surface point cloud (step S386). If cardinality of the set 226 does not exceed a predetermined cardinality threshold Tc, e.g., 20 frames (step S388), the selection process resumes as step S330. Otherwise, if the cardinality exceeds $T_C$ (step S388), the set 226 is co-registered with the 3DCT image 202. In particular, the member frames 216 in tracking space 222 $C_{tracking}$ are co-registered with the 3DCT image 202 (step S390). The US image on the display 170 is updated to reflect the latest registration (step S392). If a predetermined image-to-image registration completion criterion is met (step S394), the selection process is halted (step S396). The selection process can also be halted at any time by the user entering a halt instruction, i.e., an instruction specialized for halting the co-registration, via the user-actuatable controls 180 (step S397). On the other hand, if the predetermined image-to-image registration completion criterion is not met (step S394), the selection process continues (step S398).

Image co-registration entails: emitting energy, and responsively and dynamically acquiring images, the acquired images having a given dimensionality; selecting, repeatedly, and dynamically with the acquiring, from among the acquired images and, as a result of the selecting, changing, repeatedly, and dynamically, membership in a set of images of the given dimensionality; and, synchronously with the change, dynamically and iteratively registering the set to an image having a dimensionality higher than the given dimensionality. The co-registration is realizable with an imaging probe for the acquiring, and a tracking system for tracking a location, and orientation, of the probe, the registering being specialized for the acquiring with the probe being dynamically, during the acquiring, any one or more of angulated, rotated and translated. The registering is initialized by individual transformations of members of the set, but without need for reconstruction, of the set into an image of dimensionality higher than the given dimensionality, that derives, from the set, additional pixels external to the members.

While the invention has been illustrated and described in detail in the drawings and foregoing description, such illustration and description are to be considered illustrative or exemplary and not restrictive; the invention is not limited to the disclosed embodiments.

For example, the organ surface depicted in the frames of the set 226 can, like that of the 3D CT image, also be densely sampled in creating a point cloud for greater co-registration accuracy.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The mere fact that certain measures are recited in mutually different dependent claims does not indicate that a combination of these measures cannot be used to advantage.

What is claimed is:

1. An image co-registration device comprising:
   an imaging probe configured for emitting energy, and responsively and dynamically acquiring images, each acquired image having a given dimensionality, wherein a phase of a body cycle is detected and the acquired images are associated with the detected phase of the body cycle;
   an image selection processor configured for selecting a currently acquired image, repeatedly and dynamically with said acquiring, from among the acquired images and, as a result of said selecting, changing, repeatedly and dynamically, membership in a set of images of said dimensionality, wherein the membership in the set of images is based, at least in part, on the detected phase of the body cycle,
   said image selection processor being further configured for calculating a measure of spatial proximity between the currently acquired image and an image in said set, said selecting being based on the calculated measure, and
   said image selection processor being further configured to determine an image quality metric for at least some of the acquired images, the image quality metric comprising at least one of an entropy, an image gradient, or an image intensity; and
   an image co-registration processor configured for, synchronously with each change in the set of images, dynamically and iteratively registering said set to an image having a dimensionality higher than said given dimensionality,
   wherein said changing includes replacing an existing member of the set of images with the selected currently acquired image based at least in part on the measure of spatial proximity and the image quality metric, and
   wherein the image having the dimensionality higher than said given dimensionality is associated with the detected phase of the body cycle.

2. The device of claim 1, further comprising:
   a tracking system for tracking a location, and orientation, of said imaging probe,
   said registering being specialized for said acquiring with said imaging probe being dynamically, during said acquiring, any one or more of angulated, rotated and translated.

3. The device of claim 1, said selecting comprising deciding whether or not to include, in said set, the currently acquired image, the iterations of said registering being correspondingly responsive to instances of the deciding whether or not to include the currently acquired image in said set.

4. The device of claim 3, wherein the currently acquired image is added to the set of images.

5. The device of claim 1, said selecting comprising examining, continuously with said acquiring, said acquired images.

6. The device of claim 1, the acquired images being of an imaging modality different from that of said image having the dimensionality higher than said given dimensionality.

7. The device of claim 1, said given dimensionality being two.

8. The device of claim 1, said selecting comprising selecting ultrasound image frames from among acquired ultrasound image frames.

9. The device of claim 1, said acquired images being acquired from different locations within an object subject to examination via said acquiring.

10. The device of claim 1, wherein an iteration of the registering of said set comprises registering each image currently in said set to the image having the higher dimensionality.

11. The device of claim 1, said registering being initialized by individual transformations of members included in said set of images, but without need for reconstruction of said set of images into an image of dimensionality higher than said given dimensionality, that derives, from said set, additional pixels external to said members.

12. The device of claim 1, said registering being subject to cardinality of said set being high enough to meet a predetermined cardinality threshold.

13. The device of claim 1, configured for repeatedly, automatically and without need for user intervention, providing user feedback dynamically in synchrony with, and based on results of, the iterative registering as the registration evolves during said acquiring.

14. The device of claim 1, further comprising a user interface configured for receiving a user instruction specialized for halting said registering.

15. The device of claim 1, wherein the image selection processor or the image co-registration processor is further configured to determine whether or not a predetermined image-to-image registration completion criterion is met and for, automatically and without need for user intervention, halting said registering responsive to said determining that said criterion is met.

16. The device of claim 1, wherein the image selection processor is further configured to determine a difference between respective contents of the currently acquired image and the image in said set, and wherein the selecting from among the acquired images is based, at least in part, on the determined difference between the respective contents.

17. An image co-registration method comprising:
   emitting energy, and responsively and dynamically acquiring images, the acquired images having a given dimensionality;
   detecting a phase of a body cycle associated with the acquired images;
   selecting a currently acquired image, repeatedly and dynamically with said acquiring, from among the acquired images and, as a result of said selecting, changing, repeatedly and dynamically, membership in a set of images of said dimensionality, wherein the membership in the set of images is based, at least in part, on the detected phase of the body cycle;
   determining an image quality metric for at least some of the acquired images, the image quality metric comprising at least one of an entropy, an image gradient, or an image intensity;
   calculating a measure of spatial proximity between the currently acquired image and an image in said set, said selecting being based on the calculated measure and the image quality metric; and
   synchronously with the change, dynamically and iteratively registering said set to an image having a dimensionality higher than said given dimensionality,
   wherein said changing includes replacing an existing member of the set of images with the selected currently acquired image based at least in part on the measure of spatial proximity and the image quality metric; and
   wherein the image having the dimensionality higher than said given dimensionality is associated with the phase of the body cycle.

18. A non-transitory computer-readable medium embodying a program for image co-registration, said program having instructions executable by a processor for performing a plurality of operations, the operations comprising:
   causing an imaging probe to emit energy, and responsively and dynamically acquire images, the acquired images having a given dimensionality;
   detecting a phase of a body cycle associated with the acquired images;
   selecting a currently acquired image, repeatedly and dynamically with said acquiring, from among the acquired images and, as a result of said selecting, changing, repeatedly and dynamically, membership in a set of images of said dimensionality, wherein the membership in the set of images is based, at least in part, on the detected phase of the body cycle;
   determining an image quality metric for at least some of the acquired images, the image quality metric comprising at least one of an entropy, an image gradient, or an image intensity;
   calculating a measure of spatial proximity between the currently acquired image and an image in said set, said selecting being based on the calculated measure and the image quality metric; and,
   synchronously with the change, dynamically and iteratively registering said set to an image having a dimensionality higher than said given dimensionality,
   wherein said changing includes replacing an existing member of the set of images with the selected currently acquired image based at least in part on the measure of spatial proximity and the image quality metric; and
   wherein the image having the dimensionality higher than said given dimensionality is associated with the phase of the body cycle.

* * * * *